United States Patent [19]

Isaacson

[11] Patent Number: 4,640,295

[45] Date of Patent: Feb. 3, 1987

[54] TOCODYNAMOMETER

[75] Inventor: Philip O. Isaacson, Chanhassen, Minn.

[73] Assignee: Aequitron Medical, Inc., Minneapolis, Minn.

[21] Appl. No.: 798,162

[22] Filed: Nov. 14, 1985

[51] Int. Cl.⁴ .............................................. A61B 5/03
[52] U.S. Cl. ................................... 128/748; 128/775; 73/727; 73/746
[58] Field of Search ............. 128/637, 675, 748, 687, 128/689, 690, 775, 782; 338/4; 73/720, 721, 726, 727, 746

[56] References Cited

U.S. PATENT DOCUMENTS 2,751,476  5/1953  Statham ................................. 73/726
4,240,444 12/1980  Virgulto et al. .................... 128/690
4,279,162  7/1981  Neill et al. ............................ 73/746
4,299,129 11/1981  Ritzinger ............................. 73/746
4,354,506 10/1982  Sakaguchi et al. ................ 128/748
4,561,447 12/1985  Kawamura et al. ............... 128/687

Primary Examiner—Kyle L. Howell
Assistant Examiner—Randy Citrin
Attorney, Agent, or Firm—Paul L. Sjoquist

[57] ABSTRACT

A tocodynamometer for measuring intra-amniotic pressure through the abdominal wall of obstetric patients, including a force transducer resiliently mounted in a housing, a precompressed coil spring between the housing and an outer backplate, and an attachment on the outer backplate for fastening thereto a belt tensioner for holding the apparatus against the patient adjacent the uterine wall.

13 Claims, 7 Drawing Figures

TOCODYNAMOMETER

BACKGROUND OF THE INVENTION

The present invention relates to a device for measuring the hydrostatic pressure in the amniotic sac during various stages of pregnancy for assisting in obstetric diagnosis. More particularly, the invention relates to a tocodynamometer having a strain gauge or other similar transducer therein wherein intra-amniotic pressure may be readily measured by merely strapping the apparatus to the patient.

Hydrostatic pressure measurements in the amniotic sac during various stages of pregnancy have been measured in the past by the use of catheters, balloons and pressure transducers which have been introduced directly into the uterus for such purposes. More recently, external pressure measuring devices have been used to perform the same functions under controlled conditions. One such external pressure measurement device is described in the "Journal of Obstetrics and Gynecology", volume 64, pages 59-66 (1957). This device is referred to as a "guard-ring tocodynamometer", which utilizes a pressure transducer centered in an outer guard ring, and a housing for supporting the outer guard ring, the housing having a slot for containing an elastic belt which may be attached about a patient. The foregoing paper describes the principles of operation and use of the guard-ring tocodynamometer, and illustrates the difficulty of obtaining proper use for such a device. The belt which attaches the device to the patient must be sufficiently tightened so as to develop an inward force sufficient to flatten the abdominal surface into virtually total contact with the outer guard ring so that intra-uterine pressure variations are transmitted to the pressure transducer, but not so tightly as to create inward forces which themselves affect the intra-uterine pressure. There is a relatively narrow range of external forces which are appropriate for proper attachment and measurement, and care must be taken to attach the device to the body so as to provide inward forces within this range.

If the procedure for attaching an external pressure measuring device to a patient is too complex there will arise a high degree of risk that the pressure readings are unreliable. Further, if the attachment procedure is too complex it will tend to discourage use of such devices in cases wherein the information provided by the device could otherwise be very helpful in medical diagnosis.

There is therefore a need for a tocodynamometer which may be easily attachable to a patient, and which gives reliable pressure readings without a complex attachment procedure. Further, there is a need for a tocodynamometer which may be readily used and reused within a medical practice, and which is capable of adhering to the principles of sanitation and cleanliness which are demanded of medical instruments.

SUMMARY OF THE INVENTION

A tocodynamometer for the external measurement of intra-amniotic pressure, having a housing which resiliently supports a strain gauge force transducer, and having a backplate for coupling to a patient belt for attachment about the patient, wherein a prestressed spring is engageable between the backplate and the housing, thereby providing a preset expansion force tending to force the backplate and housing away from one another. The invention includes a means for constraining the housing and backplate in spaced relationship under the prestressing spring forces, so that the patient belt may be attached with just sufficient force to overcome the prestress force, thereby transferring to the resiliently mounted strain gauge the prestressing force. The prestressing force is selected to be of sufficient magnitude to cause the strain gauge to apply sufficient force to the patient to enable accurate pressure readings without further calibration. The invention includes an improved mounting structure for attachment of a leaf spring to the housing without introducing stresses to the strain gauge attached to the leaf spring.

It is therefore a principal object of the present invention to provide a tocodynamometer which will yield accurate pressure measurements without a complex calibration or mounting procedure.

It is another object of the present invention to provide a tocodynamometer capable of repeatable and accurate measurements without requiring a calibration procedure.

It is another object of the present invention to provide a tocodynamometer which is totally self-enclosed for sanitary and other purposes.

BRIEF DESCRIPTION OF THE DRAWINGS

The foregoing and other objects will become apparent from the following specification and claims, and with reference to the appended drawings, in which:

DESCRIPTION OF THE PREFERRED EMBODIMENT

Figure 1:
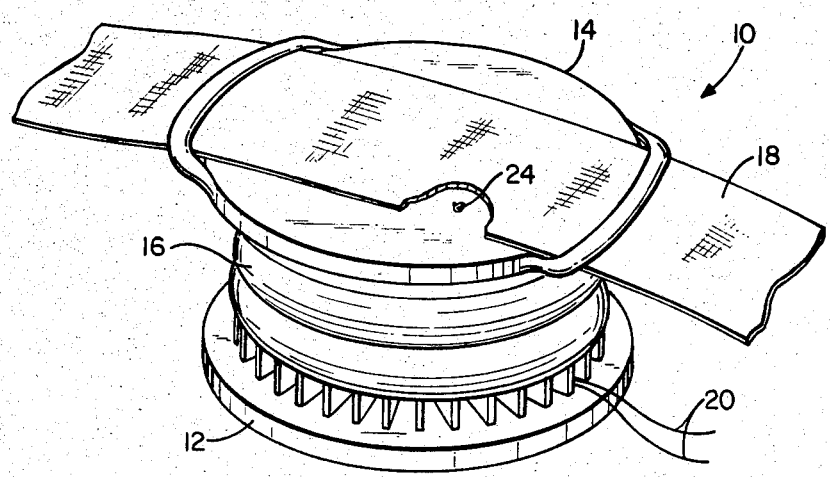
FIG. 1 shows an isometric view of the invention.

Referring first to FIG. 1, a tocodynamometer 10 is shown in isometric view. Tocodynamometer 10 includes a lower housing 12 and an upper housing 14, with an outer bellows covering 16 extending between the respective housing. A belt 18 is connected through upper housing 14, belt 18 having sufficient length for attachment about a patient. An electric signal line 20 extends from lower housing 12, and is adapted for connection to a suitable amplifier and indicator circuit (not shown).

Tocodynamometer 10 operates on the principle of utilizing resistance strain gauges affixed to a leaf spring, which spring is stressed by intra-amniotic pressure variations. The strain gauges attached to the leaf spring are resistance devices, and variations in resistance caused by pressure changes may be measured by state-of-the-art circuits, through signals carried over signal line 20. As an example of strain gauges which may be utilized in connection with tocodynamometer 10, it has been found that devices manufactured by Micro-Measurements Division of Measurements Group, Inc. of Raleigh, N.C., under Gauge Type EA-06-125BZ-350 are suitable. These strain gauges are resistance devices having an internal resistance of 350 ohms, to within an accuracy of 0.15 percent. One or more such strain gauges may be affixed to a leaf spring for producing the desired measurements, and they may be connected into, or form a part of, a balanced bridge circuit of a type which is well known in the art. One such example of a typical circuit is provided in the aforementioned paper.

Figure 2A:
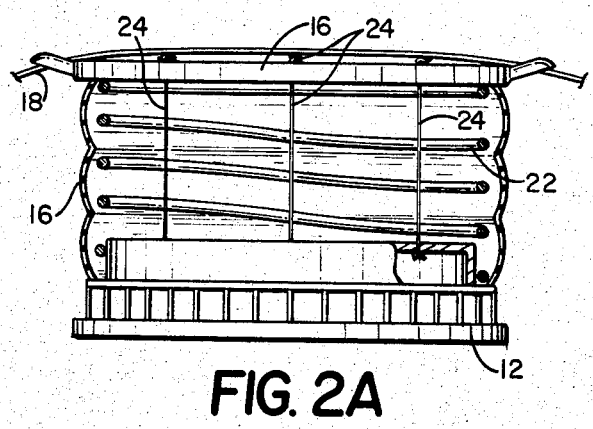
FIG. 2A shows an elevation view of the invention in partial cross section.
Figure 2B:
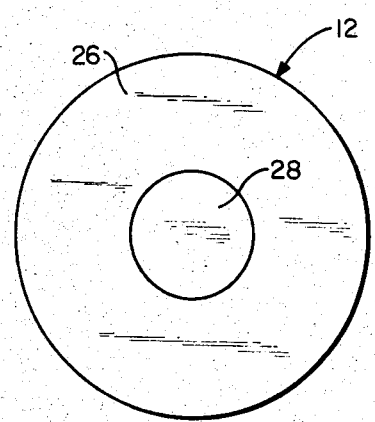
FIG. 2B shows a bottom view of the invention.

FIG. 2A shows an elevation view of tocodynamometer 10 in partial cross section. A coil spring 22 is seated between lower housing 12 and upper housing 14. Coil spring 22 is held in a precompressed condition by a plurality of cords 24 which are themselves attached between lower housing 12 and upper housing 14. Cords 24 are placed in tension by coil spring 22, which is compressed to a predetermined prestressing spring force prior to attachment of cords 24. Cords 24 may be attached by a simple knotting arrangement, or by connecting them through keyhole apertures as illustrated in FIG. 1. When cords 24 are properly connected they have a length which provides a predetermined precompression of coil spring 22, which precompression yields a predetermined outward force by coil spring 22 which is offset by equal and opposing tensile forces within cords 24. Bellows 16 is collapsible to provide an outer covering over coil spring 22 under all conditions of compression. Bellows 16 provides a protective cover about coil spring 22 in the region between lower housing 12 and upper housing 14. FIG. 2B shows a bottom view of lower housing 12, which includes an outer guard ring 26 and an inner transducer 28. Transducer 28 is movable relative to guard ring 26, and is intended to be responsive to pressure variations when the lower surface of lower housing 12 is attached against a patient's body by means of belt 18. Belt 18 provides a downward application force against tocodynamometer 10 to assure that the device is adequately facing against a patient's body.

Figure 3:
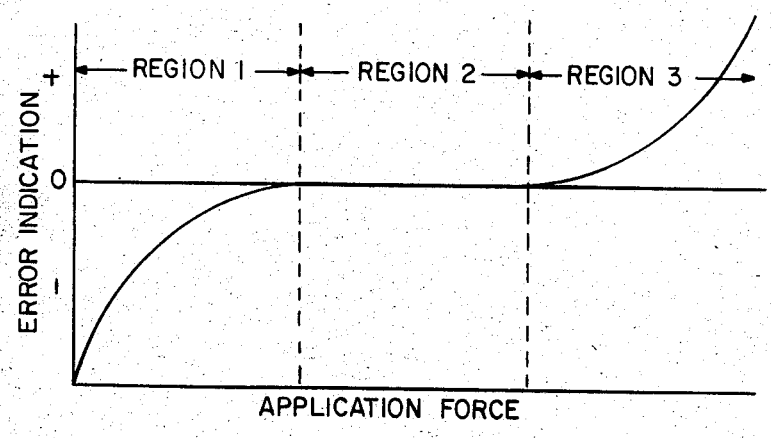
FIG. 3 shows a graph of air indication as a function of application force.

FIG. 3 shows a typical graph illustrating the relative error indication provided by tocodynamometer 10 as a function of the application force provided by belt 18. If belt 18 is too loosely attached about the patient's body, the lower surface of lower housing 12 will be insufficiently clamped against the patient's body and will therefore provide low pressure signals. This is illustrated in region 1 of the graph of FIG. 3, wherein application forces are too low to provide accurate pressure indications. If application forces, caused by tightening belt 18 too tightly about the patient's body, are too high a tocodynamometer 10 will register excessive pressure readings, as is shown in region 3 of the graph of FIG. 3. Under this condition tocodynamometer 10 is clamped so tightly about the patient's body as to compress the amniotic sac and thereby introduce increased pressure into the sac. When application forces are nominal (region 2) belt 18 is tightened sufficiently far as to provide a good coupling against the patient's body by the lower surface of lower housing 12, thereby causing transducer 28 to accurately respond to internal pressure variations.

Figure 4:
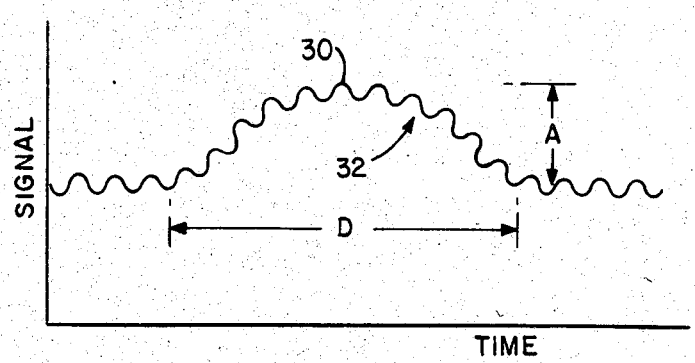
FIG. 4 shows a chart of typical signal outputs.

Under conditions of adequate application force being applied, an output signal 32 is presented over lines 20 of the type shown in FIG. 4. This signal 32 will contain periodic breathing signals 30 overriding a contraction signal which may extend over a period of one to several minutes. The contraction signal may achieve an amplitude A which is representative of the strength of the contraction, and the signal may exist over a contraction time D. The amplitude, frequency and timing of such signals are useful in the diagnosis of various conditions relating to premature birth.

Figure 5:
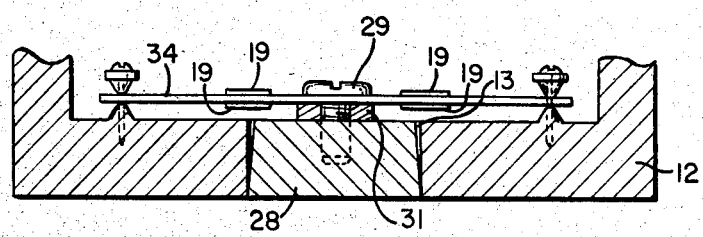
FIG. 5 shows an expanded partial cross sectional view.

FIG. 5 shows a cross sectional view of a portion of lower housing 12 and related structure. Lower housing 12 has a central opening 13, preferably having a slight conical taper from outside to inside. A transducer 28 is relatively loosely fitted in opening 13, transducer 28 preferably having a slight conical taper of reduced dimension from outside to inside. In this manner, transducer 28 is relatively freely movable within opening 13, there being provided sufficient clearance for movement of transducer 28 relative to lower housing 12, and for a small degree of canting of transducer 18 relative to lower housing 12. A leaf spring 34 is affixed at its respective ends to lower housing 12. Leaf spring 34 is affixed at its center to transducer 28 by means of a fastener 29. Leaf spring 34 has one or more resistance strain gauges 19 affixed thereto, each of the strain gauges 19 having external connections (not shown) for connecting to signal line 20. A spacer 31 may be used between leaf spring 34 and transducer 28 so as to assure a rigid connection therebetween, and strain gauges 19 will then register, in the form of resistance changes, minute deflections of leaf spring 34 caused by movement of transducer 28.

Figure 6:
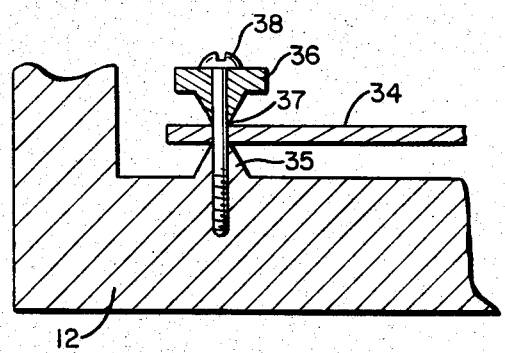
FIG. 6 shows a further expanded cross sectional view of a portion of FIG. 5.

FIG. 6 shows a further expanded view of a portion of FIG. 5, illustrating the mounting connection of leaf spring 34 against lower housing 12. A pedestal 35 is formed on lower housing 12. Pedestal 35 provides a region of reduced contact for bearing against leaf spring 34. A clamp bar 36 is affixed against leaf spring 34 and pedestal 35 by means of fastener 38. Clamp bar 36 has a raised shoulder 37 which provides a similar region of reduced contact area bearing against leaf spring 34. Leaf spring 34 is therefore clamped between two regions of point or line contact, thereby minimizing extraneous stresses which might otherwise be imposed against leaf spring 34 by a flat contact surface. Both ends of leaf spring 34 are similarly clamped, to freely suspend leaf spring 34 between respective pedestals of lower housing 12.

In operation, tocodynamometer 10 is placed adjacent the patient's body, preferably in a region which is responsive to pressure variations within the amniotic sac. Belt 18 is adjustably tightened to cause some inward compression of upper housing 14 relative to lower housing 12. The length of cords 24 have been previously adjusted so as to provide a predetermined compression force by coil spring 22 which is equal to the application force required for operation of the device in region 3 of the graph of FIG. 3. Under these conditions, when belt 18 is tightened so as to cause some compression of outer housing 14 the prestressed force of coil spring 22 is then inwardly directed against the patient's body to provide the proper amount of application force for operation in region 3. Signal line 20 is then connected to a suitable indication device for monitoring and measuring the strain gauge variations over an extended period of time. The indication device may be a strip chart recorder, a meter indicator, or some form of signal transmitter for transmission of the signal to a remote location. When connected in this manner the tocodynamometer will provide a continuous indication of pressure variations for monitoring and diagnosis as determined by competent medical personnel.

The present invention may be embodied in other specific forms without departing from the spirit or essential attributes thereof, and it is therefore desired that the present embodiment be considered in all respects as illustrative and not restrictive, reference being made to the appended claims rather than to the foregoing description to indicate the scope of the invention.

What is claimed is:

1. An apparatus for housing a pressure transducer for measuring intra-amniotic pressure through the abdominal wall of an obstetric patient, comprising
   (a) a ring-shaped housing having a smooth lower surface and a center opening therethrough;
   (b) a transducer member loosely fitted in said center opening, said transducer member having a smooth lower surface proximately aligned with said ring-shaped housing smooth lower surface;
   (c) a leaf spring having respective ends affixed to said ring-shaped housing opposite its lower surface and having a center point affixed to said transducer member, said leaf spring having one or more strain gauges affixed thereon;
   (d) an outer housing spaced away from said ring-shaped housing and a compression spring seated between said outer housing and said ring-shaped housing to bias the respective housings in spaced apart relation;
   (e) means, connected between said outer housing and said ring-shaped housing, for at least partially compressing said compression spring; and
   (f) means for attaching a belt to said outer housing.

2. The apparatus of claim 1, further comprising a compressible cover attached between respective housings and about said compression spring.

3. The apparatus of claim 2, wherein said means for at least partially compressing said compression spring further comprises at least one tension cord affixed at its respective ends to said respective housings.

4. The apparatus of claim 3, wherein said compressible cover further comprises a bellows cover.

5. The apparatus of claim 1, wherein said ring-shaped housing further comprises a pair of raised pedestals, each of said pedestals respectively positioned to support an end of said leaf spring, said pedestals having a generally rounded surface contacting said leaf spring.

6. The apparatus of claim 5, further comprising a clamp bar affixed against respective ends of said leaf spring, said clamp bar having a generally rounded surface contacting said leaf spring, and including a fastener passing through said clamp bar, said leaf spring and into said ring-shaped housing.

7. An apparatus for housing a pressure transducer for measuring intra-amniotic pressure through the abdominal wall of a patient, comprising
   (a) a lower housing having a lower surface adapted for contacting said abdominal wall; a central opening through said lower housing and a movable transducer element in said opening;
   (b) a leaf spring bridging said opening and having two ends respectively fastened to said lower housing opposite its lower surface, including means for attaching the center of said leaf spring to said movable transducer element, and including pressure transducer means attached to said leaf spring for developing signals representative of intra-amniotic pressure;
   (c) an upper housing in spaced apart relation to said lower housing, said upper housing having means for connection to a belt for attachment about said patient; and
   (d) a compression spring having one end seated in said lower housing in non-interfering relationship to said movable transducer element and said leaf spring, and having a second end seated in said upper housing, and means connected between said upper and lower housing for compressing said spring to a predetermined length which is less than its free length.

8. The apparatus of claim 7, further comprising a foldable cover about said compression spring respectively attached to said upper housing at one end and to said lower housing at another end.

9. The apparatus of claim 8, wherein said means for compressing further comprises at least one tension line attached at respective ends to said housings.

10. The apparatus of claim 9, wherein said foldable cover further comprises a bellows cover.

11. The apparatus of claim 10, wherein said lower housing further comprises an outer ring member and said movable transducer element further comprises a center piston member; said center piston member being attached to said leaf spring.

12. The apparatus of claim 11, further comprising a raised pedestal in said lower housing positioned in supporting relationship to each of two ends of said leaf spring.

13. The apparatus of claim 12, further comprising a clamping means for affixing respective ends of said leaf spring against said pedestals, said clamping means having a line contact edge bearing against said leaf spring.

* * * * *